(12) United States Patent
Vasta et al.

(10) Patent No.: US 9,750,865 B2
(45) Date of Patent: Sep. 5, 2017

(54) APPARATUS FOR EXTRACORPOREAL BLOOD TREATMENT AND A CONTROL METHOD THEREFOR

(71) Applicant: Gambro Lundia AB, Lund (SE)

(72) Inventors: Alessandro Vasta, Modena (IT); Francesco Fontanazzi, Modena (IT); Mauro Suffritti, Medolla (IT)

(73) Assignee: Gambro Lundia AB, Lund (SE)

( * ) Notice: Subject to any disclaimer, the term of this patent is extended or adjusted under 35 U.S.C. 154(b) by 338 days.

(21) Appl. No.: 14/428,257

(22) PCT Filed: Aug. 8, 2013

(86) PCT No.: PCT/IB2013/056495
§ 371 (c)(1),
(2) Date: Mar. 13, 2015

(87) PCT Pub. No.: WO2014/049459
PCT Pub. Date: Apr. 3, 2014

(65) Prior Publication Data
US 2015/0238681 A1  Aug. 27, 2015

Related U.S. Application Data

(60) Provisional application No. 61/707,463, filed on Sep. 28, 2012.

(30) Foreign Application Priority Data

Sep. 28, 2012  (EP) ..................... 12006804

(51) Int. Cl.
*A61M 1/36* (2006.01)
*A61M 1/16* (2006.01)
(Continued)

(52) U.S. Cl.
CPC ............ *A61M 1/3607* (2014.02); *A61M 1/16* (2013.01); *A61M 1/1603* (2014.02); *A61M 1/34* (2013.01);
(Continued)

(58) Field of Classification Search
CPC ........ A61M 1/16; A61M 1/1603; A61M 1/34; A61M 1/3607; A61M 1/3624;
(Continued)

(56) References Cited

U.S. PATENT DOCUMENTS 4,231,366 A  11/1980  Schael
4,570,484 A   2/1986  Sokalski
(Continued)

FOREIGN PATENT DOCUMENTS

CN  1678360  10/2005
CN  1747755   3/2006
(Continued)

OTHER PUBLICATIONS

International Search Report and Written Opinion mailed Dec. 13, 2013, for related Intl. Appln. No. PCT/IB2013/056495.
(Continued)

*Primary Examiner* — John Kim
(74) *Attorney, Agent, or Firm* — K&L Gates LLP

(57) ABSTRACT

An apparatus is described for extracorporeal blood treatment (1), comprising a treatment unit (2), an extracorporeal blood circuit (8) and a fluid evacuation line (10). The apparatus comprises a control unit (21) connected with a pressure sensor (13, 14) and with a blood pump (9) and configured to move the blood pump (9), generating a variable flow with a constant component equal to a desired blood flow value and a variable component having a nil mean value; the variable flow generates, in the expansion chamber (11, 12), a progression of the pressure that is variable over time (P(t)) with (Continued)

a pressure component (ΔP) oscillating about a mean value ($P_{avg}$). The control unit receives, from the sensor, a plurality of values ($P_j$) over a period of time (T) comprising a plurality of oscillations of the pressure about the mean value and calculates, according to the pressure values ($P_j$), a control value that is representative of the oscillating pressure component (ΔP) and then compares the control value with a reference threshold to determine the verification or not of a condition of variation of the blood level in the expansion chamber (11; 12).

18 Claims, 7 Drawing Sheets

(51) Int. Cl.
*A61M 1/34* (2006.01)
*F04B 43/12* (2006.01)

(52) U.S. Cl.
CPC ........ *A61M 1/3624* (2013.01); *A61M 1/3627* (2013.01); *F04B 43/12* (2013.01); *A61M 2205/27* (2013.01); *A61M 2205/3331* (2013.01); *A61M 2205/3389* (2013.01)

(58) Field of Classification Search
CPC ............ A61M 1/3627; A61M 2205/27; A61M 2205/3331; A61M 2205/3389; F04B 43/12
See application file for complete search history.

(56) References Cited

U.S. PATENT DOCUMENTS

| | | |
|---|---|---|
| 7,013,727 B2 | 3/2006 | Delnevo |
| 7,435,235 B2 | 10/2008 | Sternby |
| 7,435,253 B1 | 10/2008 | Sternby |
| 7,563,240 B2 | 7/2009 | Gross et al. |
| 7,985,196 B2 | 7/2011 | Kopperschmidt et al. |
| 8,091,407 B2 | 1/2012 | Schneider et al. |
| 8,430,834 B2 | 4/2013 | Kopperschmidt |
| 8,741,147 B2 | 6/2014 | Bene et al. |
| 2005/0119600 A1 | 6/2005 | Lucke et al. |

FOREIGN PATENT DOCUMENTS

| | | |
|---|---|---|
| CN | 1946441 | 4/2007 |
| CN | 101189509 | 5/2008 |
| CN | 101400387 | 4/2009 |
| CN | 101516418 | 8/2009 |
| EP | 0075606 | 4/1983 |
| EP | 2383003 | 11/2013 |
| WO | 0137899 | 5/2001 |

OTHER PUBLICATIONS

International Search Report and Written Opinion mailed Dec. 2, 2013, for related Intl. Appln. No. PCT/IB2013/056481.

APPARATUS FOR EXTRACORPOREAL BLOOD TREATMENT AND A CONTROL METHOD THEREFOR

CROSS REFERENCE TO RELATED APPLICATIONS

The present application is a National Stage of International Application No. PCT/IB2013/056495, filed on Aug. 8, 2013, which claims priority to European Patent Application No. 12006804.4, filed Sep. 28, 2012, and U.S. Provisional Application No. 61/707,463, filed Sep. 28, 2012, the entire contents of which are being incorporated herein by reference.

FIELD OF THE INVENTION

The present invention relates to an apparatus for extracorporeal blood treatment and also to a control method of the apparatus.

BACKGROUND OF THE INVENTION

Known apparatus for extracorporeal treatment of blood include at least one treatment unit (for example a dialyser or a filter, or an ultrafilter or a plasma filter or a filter unit of any other nature) having a semipermeable membrane which separates the unit of treatment into two chambers. An extracorporeal blood circuit allows the circulation of blood taken from a patient internally of the first chamber. At the same time, and typically in a countercurrent direction to the blood, a treatment fluid is circulated through a special circuit in the second chamber of the treatment unit. This type of equipment for blood treatment, known as dialysis apparatus, may be used for the removal of solutes and excess fluid from the blood of patients suffering from renal failure.

The extracorporeal blood circuit also includes two expansion chambers, also called bubble-traps, respectively located on a blood removal line from the patient and on a return blood line to the patient.

The expansion chambers, during the treatment, contain a predetermined quantity of blood up to a depth and a predetermined quantity of gas (air) in the remaining part of the chamber.

Clearly, for a safe operation of the extracorporeal treatment, the level of blood should never fall below a critical minimum level that could lead to the introduction of air into the extracorporeal circulation lines and subsequent potential infusion of the air into the circulatory system of the patient, with serious consequences.

Since the risks of such an event exist, and the problems caused to the patient are extremely serious, if not critical, the known dialysis machines are equipped with safety systems that may detect such an event and, should it occur, may place the patient in safety.

In particular, a device is in general provided on the return line blood to the patient, just before the vascular access and downstream of the venous expansion chamber, which device is directly connected to the unit control of the machine and is for the detection of air bubbles in the blood.

In the event that air is detected in the venous line, the control unit activates a patient safety procedure for the isolation of the patient by at least closing clamps on the extracorporeal blood circuit and shutting down the blood pump.

In addition to this safety device, some machines are also equipped with appropriate blood level sensors, optical or acoustic, in the venous expansion chamber (more rarely also in the arterial expansion chamber) able to signal the reaching of a minimum level that requires the intervention of specialized personnel to restore the correct quantity of blood in the chamber such as to avoid risks to the patient.

These systems, while fulfilling the tasks to which they are directed, incur additional costs and changes to the hardware of a machine on which they are or are to be installed.

Particularly because of the cost, these security systems are generally present only on the return line of the blood downstream of the dialyzer.

Furthermore, it is also worth mentioning that the bubble sensor device is generally able to reliably detect only bubbles of a certain size, while not possessing a sensitivity that would enable micro-bubbles of air dissolved in the blood to be detected.

There are recent studies (e.g. "Microemboli, developed during hemodialysis, pass the lung barrier and may cause ischemic lesions in organs such as the brain" by Ulf Forsberg, Per Jonsson, Christofer Stegmayr and Bernd Stegmayr) that have linked some typical disorders of chronic patients such as pulmonary hypertension and other ischemic problems with the quantity of air, in the form of micro-bubbles, generated by current dialysis machines and which are not disclosed by the current safety systems.

It should be noted in this regard that the generation of micro-bubbles occurs mainly because of the entry of air into the removal line, for example due to a low level of blood in the blood chamber (owing to various situations such as bad machine priming or infusion with air entry); in fact the bubbles that may get into the bloodstream and reach the dialyzer, which fragments them and makes them difficult to detect.

Also known from the U.S. Pat. No. 7,013,727 is a method for determining the blood level in a chamber of dialysis machines which exploits the ideal gas law in order to return to that level.

In particular, it exploits the change in blood volume in the chamber linked to the thrust generated on the blood by a peristaltic pump and, by means of two sensors (pressure and/or flow) the level in the chamber is detected.

This methodology, while enabling doing without a level sensor, typically requires additional hardware (a further sensor) in addition to that already present on the machine.

SUMMARY

An aim of the present invention is to disclose an apparatus for blood treatment able to detect a variation in the blood level in expansion chambers which may be an index of potential ingress of air into the extracorporeal blood circuit.

A further aim of the invention is to provide an apparatus which may perform the said monitoring operation without any need for additional hardware with respect to the hardware already present on-board the machine.

A further auxiliary aim of the described embodiment is also to enable monitoring in the arterial expansion chamber and possible also enabling monitoring in the venous expansion chamber to support the prevention systems already present in the machine.

A further aim of the described embodiment is to enable use on machines already in use in clinical structures by means of an update to the operating software.

A further auxiliary aim of the invention is to provide an apparatus able to perform this analysis reliably, lowering the false positives and increasing the detecting of the situations of risk.

At least one of the above-indicated aims is substantially attained by a blood treatment apparatus according to one of more of any of the accompanying claims.

Aspects of the invention are illustrated in the following.

In a first independent aspect of the invention, an apparatus is provided for extracorporeal blood treatment comprising: at least one treatment unit (2) having at least one first chamber (3) and at least one second chamber (4) separated from one another by a semipermeable membrane (5); at least one blood removal line (6) connected to an inlet port of a first chamber and predisposed to remove blood from a patient; at least one blood return line (7) connected to an outlet port from the first chamber and predisposed to return treated blood to the patient; at least one expansion chamber (11, 12) placed at least in one of the blood removal line (6) and the blood return line (7), the expansion chamber being arranged in use to contain a quantity of gas in an upper portion and a quantity of blood at a set level in a lower portion, the blood removal line (6), the blood return line (7), the first chamber (3) and the at least an expansion chamber (11, 12) being part of an extracorporeal blood circuit (8); at least one blood pump (9) operating at the extracorporeal blood circuit (8) to move the blood in the circuit; at least a pressure sensor (13, 14) associated to the expansion chamber (11, 12) and configured to enable determining pressure values internally of the expansion chamber (11, 12); at least one fluid evacuation line (10) connected to an outlet port of the second chamber; a control unit (21) connected to the at least one pressure sensor (13, 14), with the pump (9), and configured such as: to move the blood pump (9) to generate a variable blood flow comprising a constant flow component of a set blood flow value and a variable flow component having a substantially nil average value, the variable blood flow generating at least in the expansion chamber (11, 12) a pressure progression that is variable in time (P(t)) comprising a pressure component ($\Delta$P) oscillating about a mean value ($P_{avg}$); to receive from the at least a sensor (13, 14) a plurality of pressure values ($P_j$) for a time period (T) comprising at least one, and in particular a plurality, of pressure oscillations about the means value ($P_{avg}$), the pressure values ($P_j$) being measured at successive time instants ($t_j$); to calculate, as a function of the pressure values ($P_j$), a control value (VarP) that is representative of the oscillating pressure component ($\Delta$P), to compare the control value (VarP) representing the oscillating pressure component ($\Delta$P) with a reference threshold ($T_h$), and to determine, following the comparison, the occurrence or not of a condition of variation of the blood level in the expansion chamber (11; 12).

In a second aspect of the invention, a method is provided for detecting level variations of the blood level in expansion chambers used in apparatus for extracorporeal blood treatment and/or a method for reducing the risk of infusion microbubbles of gas into a patient in apparatus for extracorporeal blood treatment, comprising: at least one treatment unit (2) having at least one first chamber (3) and at least one second chamber (4) separated from one another by a semipermeable membrane (5); at least one blood removal line (6) connected to an inlet port of a first chamber and predisposed to remove blood from a patient; at least one blood return line (7) connected to an outlet port from the first chamber and predisposed to return treated blood to the patient; at least one expansion chamber (11, 12) placed at least in one of the blood removal line (6) and the blood return line (7), the expansion chamber being arranged in use to contain a quantity of gas in an upper portion and a quantity of blood at a set level in a lower portion, the blood removal line (6), the blood return line (7), the first chamber (3) and the at least an expansion chamber (11, 12) being part of an extracorporeal blood circuit (8); at least one blood pump (9) operating at the extracorporeal blood circuit (8) to move the blood in the circuit; at least one pressure sensor (13, 14) associated to the expansion chamber (11, 12) and configured to enable determining pressure values internally of the expansion chamber (11, 12); at least one fluid evacuation line (10) connected to an outlet port of the second chamber; the method comprising carrying out a control procedure comprising: moving the blood pump (9) to generate a variable blood flow comprising a constant flow component of a set blood flow value and a variable flow component having a substantially nil average value, the variable blood flow generating at least in the expansion chamber (11, 12) a pressure progression that is variable in time (P(t)) comprising a pressure component ($\Delta$P) oscillating about a mean value ($P_{avg}$); receiving from the at least one sensor (13, 14) a plurality of pressure values ($P_j$) for a time period (T) comprising at least one, and in particular a plurality, of pressure oscillations about the means value ($P_{avg}$), the pressure values ($P_j$) being measured at successive time instants ($t_j$); calculating, as a function of the pressure values ($P_j$), a control value (VarP) that is representative of the oscillating pressure component ($\Delta$P), comparing the control value (VarP) representing the oscillating pressure component ($\Delta$P) with a reference threshold ($T_h$), and determining, following the comparison, the occurrence or not of a condition of variation of the blood level in the expansion chamber (11; 12).

In a 3rd aspect according to any one of the preceding aspects, the condition of level variation in the blood level in the expansion chamber (11, 12) occurs when the control value (VarP) representing the oscillating pressure component ($\Delta$P) is lower than the reference threshold ($T_h$).

In a 4th aspect according to any one of the preceding aspects, the calculated control value (VarP) representing the oscillating pressure component ($\Delta$P) is a statistical indicator.

In a 5th aspect according to the preceding aspect, the statistical indicator being a dispersion index summarily describing a quantitative statistical distribution of the measure pressure values ($P_j$), in particular a control value being an indicative measurement of distance of the pressure values ($P_j$) from a central value, for example, identified with the mean pressure value ($P_{avg}$) of the pressure or with the median value of the pressure.

In a 6th aspect according to any one of the preceding aspects, the control value (VarP) representing the oscillating pressure component ($\Delta$P) is a function of the statistical variance of the measured pressure values ($P_j$).

In a 7th aspect according to the preceding aspect, the comparison step is a comparison step of the statistical variance (VarP) of the measured pressure values ($P_j$) with a reference threshold ($T_h$).

In an 8th aspect according to any one of the preceding aspects, the statistical variance (VarP) of the measured pressure values ($P_j$) is calculated on a plurality n of measured pressure values ($P_j$), in particular, n being greater than 6 and still more in particular n being at least 10.

In a 9th aspect according to any one of the preceding aspects, the reference threshold ($T_h$) is a variable threshold, in particular the reference threshold is updated in real time during a treatment time, for example at each pressure measurement ($P_j$).

In a 10th aspect according to any one of the preceding aspects, the threshold reference ($T_h$) is a variable threshold in particular according to a specific probability of generation of a set false alarm ($P_{fa}$).

In an 11th aspect according to any one of the preceding aspects, the threshold reference ($T_h$) is a variable threshold, in particular according to the oscillating pressure component ($\Delta P$).

In a 12th aspect according to any one of the preceding aspects, the threshold reference ($T_h$) is a variable threshold according to a dispersion index summarily describing a quantitative statistical distribution of the measured pressure values ($P_j$), in particular the threshold reference being an indicative measurement of the distance of the pressure values ($P_j$) from a central value, for example, identified with the mean value of the pressure ($P_{avg}$) or the pressure median.

In a 13th aspect according to any one of the preceding aspects, the threshold reference ($T_h$) is variable in accordance with the standard deviation ($\sigma$) of the measured pressure values ($P_j$).

In a 14th aspect according to any one of the preceding aspects, the threshold value ($T_h$) is variable as a function of the confidence interval (t$\alpha$) of a Student probability distribution, in particular with n−1 degrees of freedom corresponding to a type I error $\alpha$.

In a 15th aspect according to the preceding aspect, the type I error $\alpha$ is calculated through of the following relation:

$$\alpha = 1 - \sqrt[K_n]{1 - P_{fa}}$$

in which: $K_n$=number of measurements carried out during a treatment time ($T_{tot}$); $P_{fa}$=set probability of detecting an erroneous change in blood level in the expansion chamber during a treatment time ($T_{tot}$).

In a 16th aspect according to any one of the preceding aspects, the threshold reference ($T_h$) is variable as a function of the mean ($VarP_{ref}$) of the variance (VarP) of the measured pressure values ($P_j$), in particular at the start of the treatment time.

In a 17th aspect according to any one of the preceding aspects, the threshold reference ($T_h$) is defined by the following function:

$$T_h \sqrt{VarP_{ref}} - t\alpha * \sigma$$

in which: '$VarP_{ref}$' is the mean of the variance of a number n of initial pressure values ($P_j$) measured at the start of treatment; 't$\alpha$' is the confidence interval of a Student probability distribution with n−1 degrees of freedom corresponding to a type I error $\alpha$; '$\sigma$' is the standard deviation of the pressure variance calculated on a number n of sampled pressure data ($P_j$).

In an 18th aspect according to the preceding aspects, the expansion chamber is an arterial expansion chamber (11) located on the blood removal line (6).

In a 19th aspect according to the preceding aspects, the blood pump (9) is located downstream of the arterial expansion chamber (11) along a blood transit direction.

In a 20th aspect according to any one of the preceding aspects, the expansion chamber is venous expansion chamber (12) located on the blood return line (7).

In a 21st aspect according to any one of the preceding aspects, the control procedure (or the control unit (21)) performs the steps of aspects 1 or 2, in relation to an arterial expansion chamber (11) located on the blood return line (6).

In a 22nd aspect according to any one of the preceding aspects, the control procedure (or control unit (21)) carries out the steps of aspects 1 or 2 in relation to a venous expansion chamber (12) located on the blood return line (7).

In a 23rd aspect according to the preceding aspect, the control procedure (or control unit (21)) carries out the steps of aspects 1 or 2 in relation both to an arterial expansion chamber (11) located on the blood removal line (6) and to a venous expansion chamber (12) located on the blood return line (7).

In a 24th aspect according to any one of the preceding aspects, the blood pump (9) is a peristaltic pump.

In a 25th aspect according to any one of the preceding aspects, the pressure sensor (13, 14) is located in the expansion chamber (11; 12), in particular at the portion arranged in use to contain the gas.

In a 26th aspect according to any one of the preceding aspects, the expansion chamber (11, 12) exhibits an inlet (11a, 12a) for the blood in fluid connection with the extracorporeal circuit (8) to receive, in use, blood in inlet to the chamber and an outlet (11b, 12b) for the blood in fluid connection with the extracorporeal circuit (8) to cause to flow, in use, blood in outlet from the chamber, the inlet (11a, 12a) and the outlet (11b, 12b) being positioned at a base portion of the expansion chamber (11, 12) arranged, in use, to be facing downwards and in particular always occupied by the blood.

In a 27th aspect according to any one of the preceding aspects, the expansion chamber (11, 12) exhibits a ventilation opening (15, 16) configured to allow, in use, a passage of gas from to towards the expansion chamber (11, 12), the apparatus further comprising at least an actuator (17, 18) operating on the ventilation opening (15, 16) to selectively inhibit or enable the passage of gas, the ventilation opening (15, 16) being in particular positioned at an upper portion of the expansion chamber (11, 12) arranged, in use, to be facing upwards, and still more in particular arranged to be always occupied by the gas.

In a 28th aspect according to the preceding aspect, the control procedure (or control unit 21), in the event of a verification of a number of conditions of variation of the blood level in the expansion chamber (11, 12), commands the actuator (17, 18) to enable passage of gas through the ventilation opening (15, 16).

In a 29th aspect according to the preceding aspect, the control procedure (or control unit 21) in the event of a number of conditions of variation of the blood level in the expansion chamber (11, 12), commands the actuator (17, 18) to enable passage of gas in exit from the ventilation opening (15, 16).

In a 30th aspect according to the preceding aspects, the control procedure (or control unit 21) in the event of a verification of a number of conditions of variation of the blood level in the expansion chamber (11, 12), commands actuators active at least on the extracorporeal blood circuit (8) to place the patient in a safe situation.

In a 31st aspect according to the preceding aspects, the control procedure (or control unit 21) in the event of a verification of a number of variations in the blood level contemporaneously in the expansion chamber (11, 12), commands at least the blood pump (9) to reduce or zero the blood flow in the extracorporeal blood circuit (8) and substantially annul the passage of fluid through the semipermeable membrane (5) of the treatment unit (2).

In a 32nd aspect according to the preceding aspects, the control procedure (or control unit 21) in the event of a verification of a number of variations in the blood level contemporaneously in the arterial (11) and venous (12) chambers, commands actuators active at least on the extracorporeal blood circuit (8) to place the patient in a safety condition.

In a 33rd aspect according to any one of the preceding aspects, the control procedure (or the control unit (21)) in the event of verification of a number of conditions of variation of blood level in the arterial and venous expansion chamber (11, 12), commands at least the blood pump (9) to reduce or zero the blood flow in the extracorporeal blood circuit (8) and substantially annul the fluid passage through the semipermeable membrane (5) of the treatment unit (2).

In a 34th aspect according to any one of the preceding aspects, the control procedure (or control unit (21)) moves at least the blood pump (9) before start of a treatment to create, in the expansion chamber (11, 12), the set blood level in the lower portion and to confine a complementary quantity of gas in the upper portion.

In a 35th aspect according to any one of the preceding aspects, the apparatus comprises at least a device (19) for detecting air bubbles in the blood placed on the extracorporeal blood circuit (8), the device (19) being in particular located on the blood return line (7) and still more in particular downstream of a venous expansion chamber (12) along the blood flow direction in the extracorporeal circuit.

In a 36th aspect according to any one of the preceding aspects, the apparatus further comprises at least an intercept organ of the blood flow (20, 22) active on the extracorporeal circuit (8) downstream of a venous expansion chamber (12) along the blood flow direction in the extracorporeal circuit.

In a 37th aspect according to the preceding aspect, the apparatus further comprises two intercept organs of the blood flow (20, 22) active on the extracorporeal circuit (8), one (22) downstream of a venous expansion chamber (12) along the flow direction of the blood in the extracorporeal circuit, the other (20) upstream of an arterial expansion chamber (11), in particular each of the blood flow intercept organs (20, 22) comprising a respective clamp respectively active on the blood return line (7) and on the blood removal line (6), the control unit (21) being active on the intercept organs (20, 22) to command the intercepting or not of the flow.

In a 38th aspect according to any one of the preceding aspects, the control procedure (or control unit (21)) is programmed to compare the control value (VarP) with at least a maximum admissible value (VarPmax) and a minimum admissible value (VarPmin) in order to determine whether the control value is internal of a correct functioning interval (VarP≤VarPmax; VarP≥VarPmin) and to signal a malfunction in the event that a control value falls outside of a correct functioning interval.

DESCRIPTION OF THE DRAWINGS

Some drawings are provided by way of non-limiting example, related to aspects of the invention.
In particular.

DETAILED DESCRIPTION

With reference to the accompanying drawings, 1 denotes in an apparatus for the extracorporeal treatment of blood.

The apparatus 1 comprises an extracorporeal circuit arranged to extract blood from the cardiovascular system of a subject, for example a patient P, and return the treated blood to the patient.

Figure 1:
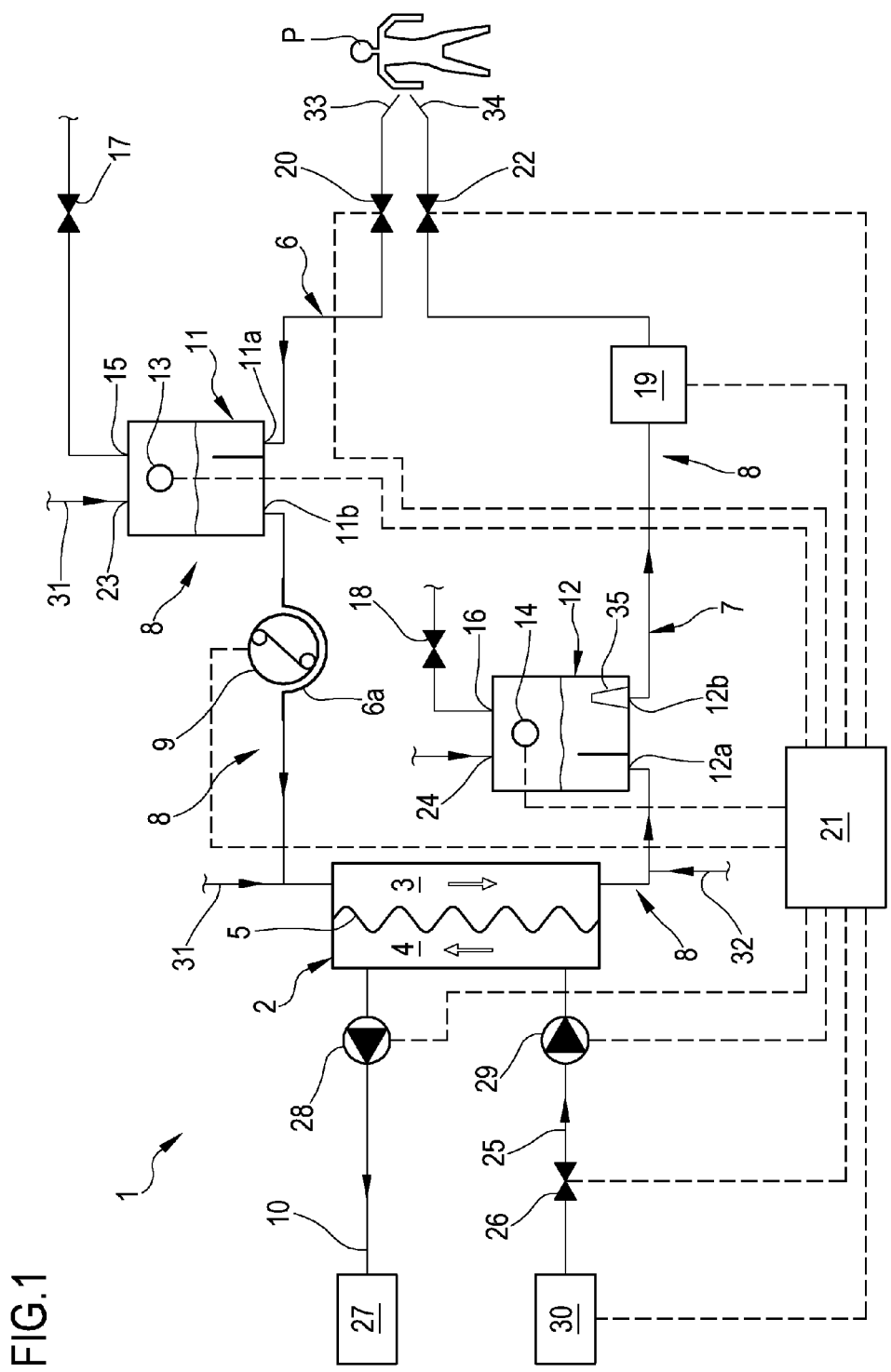
FIG. 1 schematically illustrates a blood treatment apparatus, according to the invention.

Below some possible examples are described relating to the general structure of the apparatus 1: in particular some configurations of the extracorporeal blood circuit are described, as well as the infusion lines, if present, in which a replacement fluid circulates, any dialysis line in which a dialysis fluid circulates, and the waste fluid discharge line. With reference to FIG. 1, the apparatus for the extracorporeal treatment of blood comprises at least a treatment unit 2, for example a hemofilter, a hemodiafilter, a plasmafilter, a dialysis filter, a membrane oxygenator or other units also suitable for processing the blood taken from the patient, having at least a first chamber and at least a second chamber 3 and 4 separated from one another by a semipermeable membrane 5. A blood removal line 6 is connected to an inlet port 11a of the first chamber 3 and is predisposed, in operative conditions of connection to a patient, to remove blood from a vascular access inserted, for example in a fistula on the patient. A blood return line 7 connected to an outlet port 11b of the first chamber is predisposed to receive the treated blood from the treatment unit and to return the treated blood to a further vascular access also connected to the fistula of the patient. Note that the configuration of the vascular access may be of any nature: for example, a catheter, a port implanted in the patient, a cannula, a needle, and so on.

Figure 2:
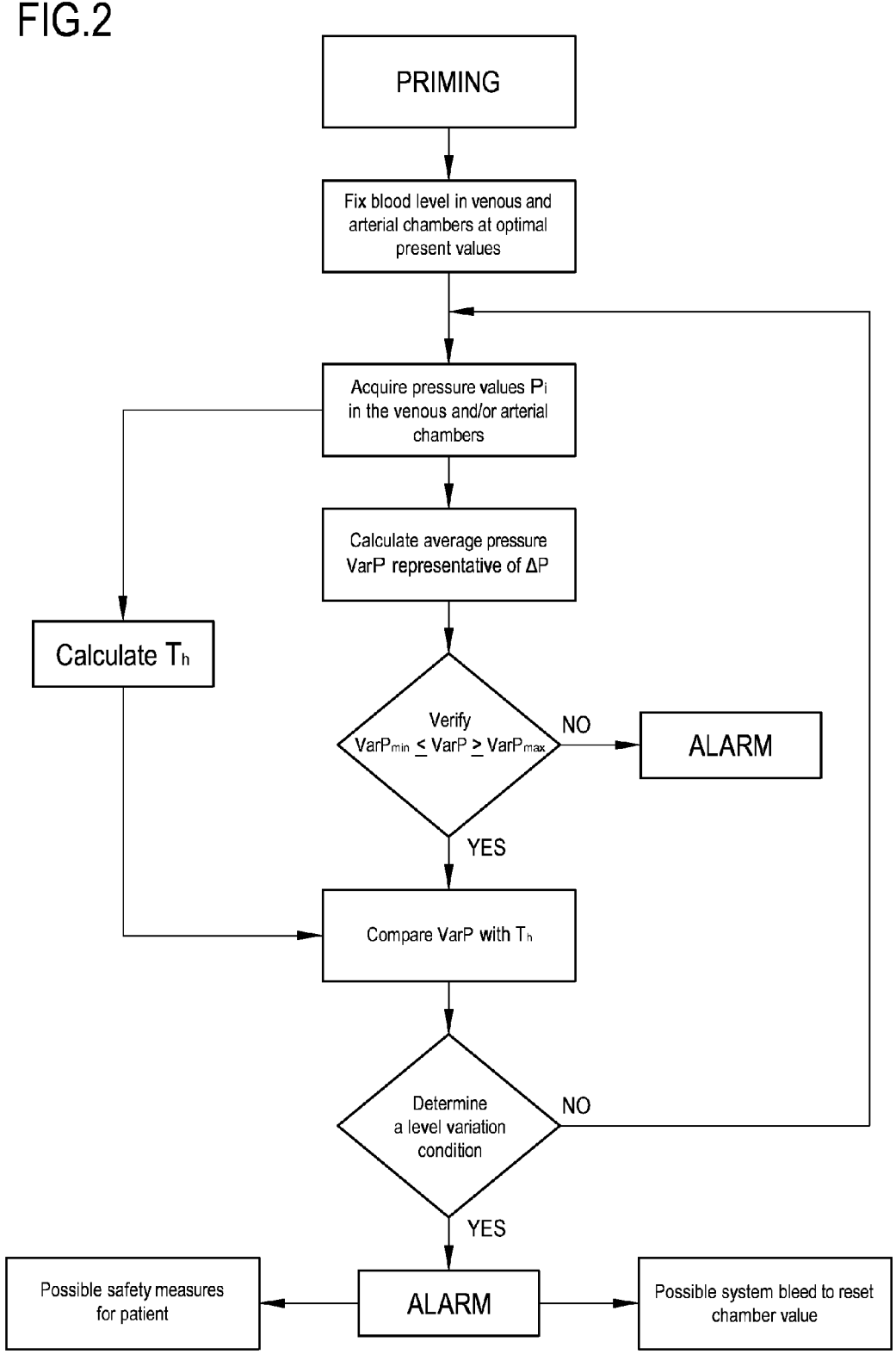
FIG. 2 is a flow diagram illustrating a control procedure according to an aspect of the invention, performable by the control unit of an apparatus for example of the type shown in FIG. 1.
Figure 3:
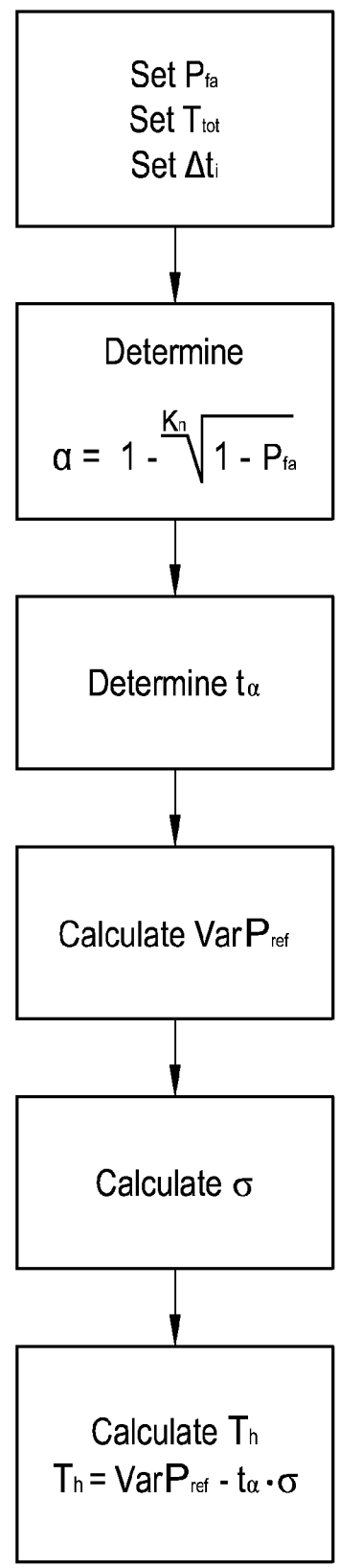
FIG. 3 is a flow diagram which illustrates the calculation of the variable reference threshold.

As can be seen in FIG. 1, the apparatus 1 comprises at least a first actuator, in the present example a blood pump 9, which operates at a blood removal line such as to facilitate the movement of the blood removed from the patient from the first end 33 of the removal line 6 connected to the patient P to the first chamber 3; the blood pump 9 is, for example, an active peristaltic pump, as shown in FIGS. 1 and 2, on a respective tube section 6a and able, when moved in a clockwise direction, to move a flow of blood along the removal line towards the first chamber 3 (see the arrows indicating the flow along this line). It should be noted that for the purposes of the present description and the appended claims, the terms "upstream" and "downstream" may be used with reference to the relative positions assumed by components belonging to or operating on the extracorporeal circuit. These terms are to be understood with reference to a blood flow direction from the first end 33 of the removal line 6 connected to the patient P towards the first chamber 3 and then towards the second end 34 of the return line 7 connected to the vascular access of the patient P.

In the example of FIG. 1, the extracorporeal circuit comprises at least an expansion chamber 11 acting on the arterial blood removal line 6 from the patient P and arranged upstream with respect to the first chamber 3 and upstream with respect to the blood pump 9.

This chamber 11 receives the blood directly from the patient and accumulates a set amount that will remain substantially constant throughout the treatment.

The extracorporeal circuit also comprises at least a venous expansion chamber 12 which operates on the venous blood return line 7, downstream of the first chamber 3 and upstream of the vascular access that returns the blood to the patient P.

At least a pressure sensor 13 is configured to detect at least a parameter relating to the pressure of the fluid present in the arterial expansion chamber 11 and a pressure sensor 14 is configured to detect at least a parameter relating to the pressure of the fluid present in the venous expansion chamber 12.

In general, the sensors 13, 14 are configured to emit a respective signal corresponding to a measured value of the parameter, then forwarding it to a control unit 21 each time a measurement is carried out in successive moments of time $t_j$. Note that it is possible to perform the detection of the pressure parameter also in close proximity of the arterial or venous expansion chambers 11, 12, for example through of a transducer located either in the section of pipe between the expansion chamber 11 and the arterial blood pump 9, or in the stretch of piping between the expansion chamber 11 and the arterial vascular access to the patient P, or in the section of pipe between the expansion chamber 12 and the venous return vascular access to the patient P or in the section of pipe between the first chamber 3 and the venous expansion chamber 12.

In any case, in a possible proper positioning of the pressure sensors 13, 14, the pressure sensors 13, 14 are directly active in the corresponding expansion chamber 11; 12 at an upper portion thereof where normally (in use) a gas (air) is housed.

It should be noted in fact that the arterial and the venous expansion chambers 11, 12 are generally arranged in use and during treatment to accommodate a predetermined amount of gas in an upper portion and a predetermined amount of blood at a predetermined level in a lower portion thereof.

Each of the expansion chambers 11, 12 has an inlet 11a, 12a for the blood that is in fluid connection respectively with a first part of removal line 6 connected to the vascular access of the patient P and with a return line portion downstream the treatment unit 2.

The chambers 11 receive blood entering through the inlets 11a, 12a. In general, the inlets 11a, 12a may be positioned at a base portion of the corresponding expansion chamber arranged, in use, to be directed downwards and in particular always occupied by blood.

In an embodiment the inlets may be connected to a respective channel internal of the arterial and venous expansion chambers 11, 12 which has an outlet in the chamber itself at a height with respect to the base.

Each of the arterial and venous expansion chambers also includes a respective outlet 11b; 12b for the blood in fluid connection with the extracorporeal circuit 8, which causes, in use, the flow of blood in outlet from the chambers. The outlets 11b, 12b are also positioned at a base portion of the respective expansion chamber 11; 12 arranged, in use, to be directed downwards and in particular always occupied by blood.

The portion of the removal line 6 which connects the outlet 11b of the arterial expansion chamber 11 to the first chamber 3 of the treatment unit 2 comprises a pump section 6a which is engaged by the peristaltic pump 9 such as, through squeezing the same tract of tube, to move the blood in the extracorporeal circuit.

A particular type of peristaltic pump 9 may be provided with two squeezing bodies (rollers) that act on the pump portion 6a twice for each rotation of the blood pump 9.

The venous chamber 12 also internally houses a venous filter 35 which separates the outlet 12b from the remaining volume of the chamber 12. The venous filter 35 helps avoiding air bubbles reaching the patient since bigger bubbles are broken and the generated small air bubbles trapped in the venous chamber.

Each of the expansion chambers 11, 12 has also a ventilation opening 15, 16 configured to allow, in use, a passage of gas into or from the expansion chamber 11; 12 itself, for example to or from the external environment.

The apparatus further comprises at least an actuator 17; 18 for each chamber 11; 12 operating on the ventilation opening 15; 16 (for example a piping connected thereto) for selectively inhibiting or enabling the passage of gas. The ventilation opening 15; 16 is in particular positioned at an upper portion of the expansion chamber 11; 12 intended, in use, to be facing upward, and even more in particular intended to be always occupied by the gas.

The actuator 17; 18 may be an air pump or even a simple clamp (or other obturator) or may be controlled (or not) by a control unit 21 for allowing gas venting should it be required.

Each of the arterial and venous expansion chamber 11, 12 may also possibly include a further access 23, 24 (service access) for receiving further fluids, medicaments or other substances in the chamber.

In relation to the set level of blood in the arterial and venous expansion chambers 11, 12, it should be noted that in general this level should be within a range of depths between a minimum value and a maximum value (possibly and in general the minimum value and a maximum value of the venous chamber 12 are different from the maximum and minimum levels of the arterial expansion chamber). Within these blood level values in the chamber it may be assumed that the equipment is working in a safe state: below, or above the minimum and maximum levels, and particularly during treatment, problems of various natures may arise, which will be more precisely described in the following.

Not least, it should also be noted out that at least one and generally both the arterial and venous expansion chambers 11, 12 have a constant containment volume, i.e. the chambers, in detail, are made of a rigid and substantially non-deformable material.

The apparatus 1 further comprises a first fluid flow intercept organ 20 operating on the removal line 6 upstream of the blood pump 9 and the arterial expansion chamber 11 and at least a second fluid flow intercept organ 22 operating in the return line 7 of the blood to the patient downstream of the venous expansion chamber 12. The intercept organs 20, 22, for example each constituted by a respective clamp controlled by the control unit 21, are arranged in the vicinity of the ends 33, 34 of the respective lines connectable to the patient P.

The apparatus may also include an air-bubble sensor 19 connected to the control unit 21 and capable of generating a signal that, if above a threshold, determines the generation of a closing command of the intercept member 22 and shuts down the blood pump 9. In particular the device 19 is located on the blood return line 7, and still more in particular downstream of the venous expansion chamber 12 along the blood flow direction in the extracorporeal circuit.

In practice, the blood removal line 6, the arterial expansion chamber 11, the first chamber 3 of the treatment unit, the return line 7 of the blood to the patient and the venous expansion chamber 12 are part of an extracorporeal blood circuit 8, which, during use of the apparatus 1, provides for the circulation of blood externally of the body of the patient undergoing treatment.

The apparatus 1 further comprises at least a fluid evacuation line 10 connected with an outlet port of the second chamber 4 such as to receive at least a filtered fluid through the semipermeable membrane 5.

The evacuation line receives the waste fluid coming from the second chamber of the unit 2, for example, comprising used dialysis liquid and/or ultrafiltered liquid through the membrane 5.

The evacuation line 10 leads to a receiving element 27, for example consisting of a collection bag or a drainage pipe for the waste fluid. One or more dialysate pumps 28 may operate on the evacuation line 10: for example in the accompanying drawings a pump 28 active on the line 10 is provided. Note that the structure of the evacuation line may also be different to the one illustrated (as long as it may properly drain the fluid exiting from the second chamber 4): for example the evacuation line 10 may comprise a single line as shown in the accompanying figures or a main drainage line and an ultrafiltration line branching from the main discharge line and provided with a respective pump (solution not shown).

In the example of FIG. 1, a dialysis line 25 is also present, for supplying a fresh treatment fluid in inlet to the second chamber 4: the presence of this line is not strictly necessary since, in the absence of the line 25, the apparatus is still able to perform treatments such as ultrafiltration, hemofiltration or plasmafiltration. In the case in which the dialysis line 25 is present, a fluid intercept organ 26 may be used to selectively allow or inhibit fluid passage through the dialysis line 25, depending on whether or not a purification by diffusive effect is to be performed inside the treatment unit.

The dialysis line 25, if present, is typically equipped with dialysis pump 29 and is able to receive a fresh fluid from a module 30, for example a bag or a section of on-line preparation of dialysis fluid, and to send such a fluid in inlet into the second chamber 4. Finally, the apparatus 1 may comprise one or more infusion lines of a replacement fluid: for example an infusion line 31 may be provided connected to the removal line 6 and/or an infusion line 32 connected to the blood return line 7. The pre- and/or post-infusion lines 31, 32 may be supplied by suitable bags or directly by the fresh dialysis fluid prepared on-line.

These lines are only schematically represented in the accompanying figures.

The apparatus is also provided with at least a control unit 21. The control unit 21 may comprise one or more digital modules, for example of the microprocessor type, or one or more analog modules, or a suitable combination of digital and analog.

As illustrated in the example of FIG. 1, the control unit 21 is connected with the blood pump 9 and/or with the dialysate pump 28 and/or with the dialysis pump 29, as well as with the pressure sensors 13, 14 of the arterial and venous expansion chambers 11, 12 and optionally, if present, with auxiliary pressure sensors. In addition the control unit may be connected to the fluid intercept organs 20, 22 and, if present, 25.

The control unit 21 is also in communication with the bubble detection device 19, with the module 30 (if the preparation is on-line) and possibly with the actuators 17, 18 on the ventilation lines 15 and 16.

The control unit 21 is configured or programmed to perform the procedures described below. If the control unit is of the programmable type, this unit is connected with a data carrier for storing instructions that, when performed by the control unit, carry out the procedures described below. The data carrier may comprise a mass storage, for example, optical or magnetic, a re-programmable memory (EPROM, FLASH) or a memory of another type.

In general, before start of treatment, the apparatus 1 is subjected to a priming procedure controlled by the control unit 21.

In particular, prior to treatment, a saline solution is fed into the extracorporeal circuit to wash and remove any air and residual particles.

At the end of this procedure, a set level of saline at the working pressure is established in the arterial and venous expansion chambers 11, 12.

Once the patient is connected to the equipment via the vascular access, the control unit 21 is configured to move at least the blood pump 9 at the beginning of a treatment to create, in the expansion chambers 11, 12, a corresponding set blood level in the lower portion, while confining a complementary quantity of gas in the upper portion.

The treatment at this point continues for the duration $T_{tot}$ required in order to appropriately treat the blood taken from the patient P.

Throughout the treatment the blood level in the arterial and venous expansion chambers 11, 12 continuously changes (although by small amounts) at least as a result of the fact that the control unit 21 moves the blood pump 9 to generate a variable flow of blood comprising a constant flow component equal to a desired blood flow value and a variable flow component at substantially zero average value. This is due in particular to the fact that the blood pump is peristaltic in nature and therefore produces a non-constant flow of blood in the circuit, as it is related to the successive squeezing actions of the pump section 6a by the roller/rollers associated to the pump rotor.

In other words, the hydraulic head of the treated fluid is given by a constriction which runs along the tube. In the described example, the pump 9 is constituted by a rotor to which two (or more rollers) are applied, which rotate to "squeeze" the tube and cause the advancement of the fluid.

Alternatively linear peristaltic pumps may be used (for example, "finger" pumps) or also other actuators capable of generating a pulsating movement in the blood, i.e. a non-constant flow, but oscillating about an average flow value.

Alternatively the control unit might control the pump to generate the pulsating movement in the blood in order to use other kinds of pumps which do not have the pressure variations inherently generated.

Consequently the variable blood flow generates in the expansion chamber (both arterial 11 and venous 12) a pressure trend that is time-variable P(t) comprising a pressure component ΔP(t) oscillating about an average value $P_{avg}$.

Figure 5:
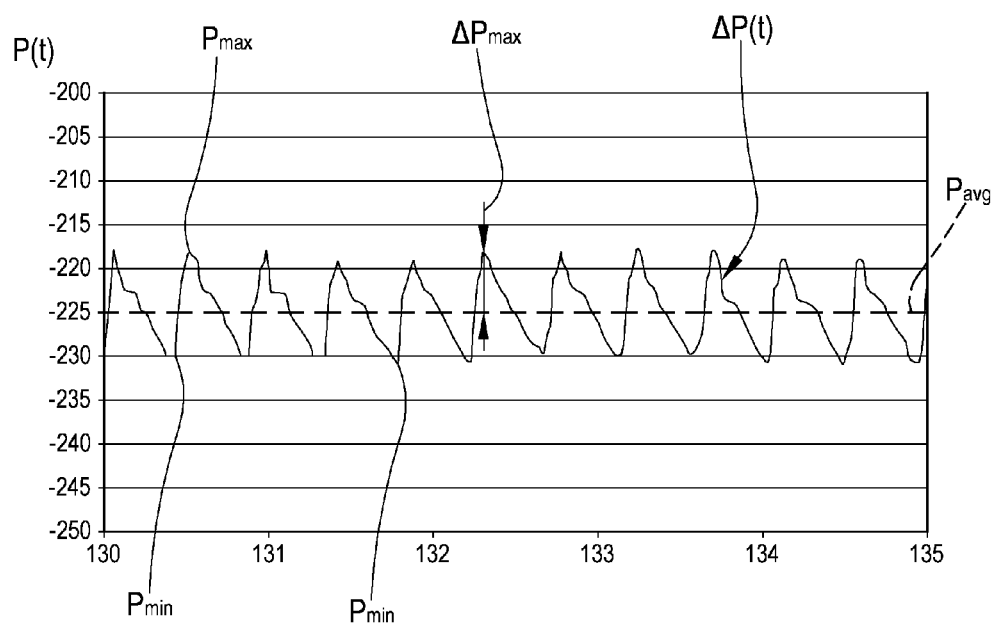
FIG. 5 shows the progression in the arterial chamber in the third condition of FIG. 4 and in a larger-scale view.

An example of the pressure trend in an arterial chamber is shown in FIG. 5 where, the measurements performed by the pressure sensor 13 over a short time interval are represented.

This graph shows the average pressure $P_{avg}$ and the oscillatory behaviour (non-symmetrical, but at a substantially zero mean value) of the pressure ΔP(t) may clearly be observed, i.e. the oscillating component of the pressure.

The control unit 21 is programmed to receive, from the pressure sensors 13, 14 located in the respective chambers, a plurality of pressure values $P_j$ for a period of time T (typically coinciding with the treatment period).

For the purposes of the implementation of the present invention, the minimum time period $T_{min}$ for which the detected pressure data $P_j$ are used, comprises at least one and in particular a plurality of oscillations of the pressure about the average value $P_{avg}$; in particular, time periods of 7 oscillations are used for each control value calculation (described in the following).

Obviously the pressure values $P_j$ are measured in discrete and successive time instants $t_j$. The sampling timing may be constant, depending on the type of pressure sensor used and possibly other parameters of apparatus operation.

The underlying principle implemented by the control unit 21, and described below in detail, is to use the pressure component $P_j$ measured at various instants $t_j$ in order to assess the level variations of blood in the expansion chamber; also verification may be made of the permanence at a set level or in any case a safety level that substantially ensures the absence of air invasion into the removal and/or return lines 6, 7.

In other terms, by filtering the level of the pressure signal of the constant value component $P_{avg}$, and using only the oscillating pressure signal, a monitoring of the permanence of the blood level in the expansion chamber at levels considered safe.

Figure 4:
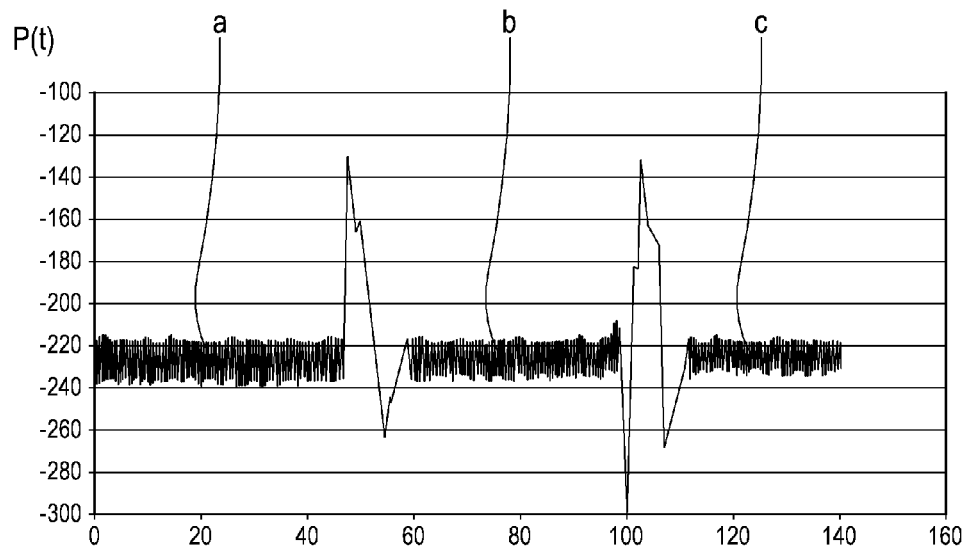
FIG. 4 is a time diagram which shows the progression of the pressure in the arterial expansion chamber in three different conditions: a first condition of standard blood level (case a), a second average blood level condition (case b) and a third condition with substantially empty chamber or low blood level (case c)

By observing in particular FIG. 4, three distinct progressions over time of the pressure signals $P_j$ detected in the arterial chamber 11 are represented in three different blood level situations: a first standard level situation, a second average level and a third minimum—or a non-safe—level situation (all illustrated in FIG. 4).

As can qualitatively be noted, the three pressure signals differ from one another and by performing an appropriate analysis thereon it is possible to determine whether or not a condition of variation of the blood level is established in any (including both) of the expansion chambers 11 and 12.

In particular the applicant has surprisingly found that the oscillating component of the pressure ΔP(t) is alone usable for the above-described verification.

For this purpose, the control unit 21 is generally set up to calculate, according to the pressure values $P_j$ received from one of the respective pressure sensors 13, 14, a control value (called VarP) which is representative of the oscillating pressure component ΔP(t). This control value VarP representing the oscillating pressure component ΔP(t) is compared with a reference threshold $T_h$ and, following the comparison, a verification is made as to whether there occurs an appreciable variation in the blood level in the respective expansion chamber 11, 12.

FIG. 5 shows how, on a variation of the blood level in the arterial expansion chamber 11, both the constant pressure component $P_{avg}$, and the oscillating pressure component ΔP(t) change.

Figure 6:
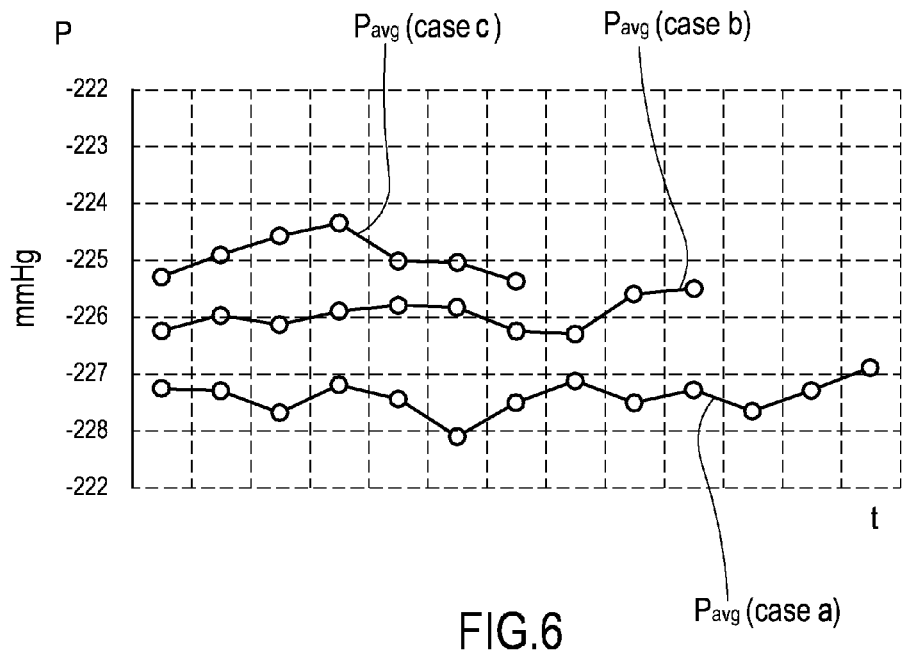
FIG. 6 is a time diagram which shows three progressions of the average arterial pressure in the arterial expansion chamber in the three respective conditions of FIG. 4.

FIG. 6 in particular illustrates the variation in the average pressure component $P_{avg}$ in the three cases of different level of FIG. 4.

Returning to FIG. 4, it may be seen how the maximum and minimum values of ΔP(t) in the three conditions vary, in particular by reducing the maximum amplitude $ΔP_{max}$ of pressure oscillation ΔP(t) (i.e. the different between the maximum peak $P_{max}$ and the minimum $P_{min}$ of each single oscillation) from the standard level situation to the minimum, or safety, level.

In these terms, the control value VarP might be, for example, the maximum amplitude $ΔP_{max}$ between the maximum peak $P_{max}$ (or minimum peak $P_{min}$) and the average pressure $P_{avg}$ of each single oscillation (or a proportional value thereto) or, alternatively, a statistical variable of the value such as for example an average of the maximum amplitudes $ΔP_{max}$ of a number of contiguous oscillations (not necessarily, but in particular, consecutive) of pressure.

The applicant has however observed that this type of absolute control value (i.e. a value linked to the absolute measurements of maximum and minimum pressure subtracted from one another to eliminate the average pressure component), though offering a clear indication of level variation, and being able therefore to be used as an indicator, is susceptible to improvement in an auxiliary aspect of the invention.

Indeed the measurement of the peak pressure values $P_{max}$ and $P_{min}$ involves the onset of problems of calculation (that may be overcome). It is clear that it is necessary, firstly, to determine which are the maximum and minimum points in situations of oscillating pressure and with measured pressure values that are discrete (each time interval $t_j$) and further the measurement is obviously subject to noise and errors of detection, which set a problem to take into account.

In this situation the use of a calculated control value VarP (representing the oscillating pressure component ΔP(t)) which is a statistical indicator appears to simplify the analysis.

In particular, the use of a statistical indicator that is an index of dispersion summarily describing a quantitative statistical distribution of the measure pressure values $P_j$ is more proper; in particular the control value is an indicative measurement of the distance of the pressure values $P_j$ from a central value, for example, identified with the average value $P_{avg}$ of the pressure or the median value of the pressure.

By operating in this way it becomes irrelevant to establish what are the maxima and minima of the pressure detected in the window of time established for the analysis, as substantially each measured value $P_j$ contributes to determining the control value VarP (it might be decided to discard some measured pressure values, for example, as clearly erroneous—greater than or less than $P_{max-admissible}$ or less than $P_{min-admissible}$ or not to consider all the values measured on the basis of other calculation optimization logics).

In the case now described VarP, representing the oscillating pressure component ΔP(t) is a function of the statistical variance of the measured pressure values $P_j$ and in detail coincides with the statistical variance.

Alternatively, other indicators may be used, such as the standard quadratic deviation, field or interval of variation, absolute standard deviation, standard deviation, median absolute deviation, interquartile deviation, Poisson dispersion index.

In relation to the step of comparison, the control unit 21 determines the verification of the condition of variation of the blood level in the expansion chamber 11 or 12 when the control value VarP representing the oscillating pressure component ΔP(t) is lower than the reference threshold $T_h$.

In detail (and as mentioned), in the formulation used, but not limitedly, the control unit 21 performs the step of comparing the statistical variance VarP of the measured pressure values $P_j$ with the reference threshold $T_h$ determining in particular whether VarP is lower or not than the threshold $T_h$.

Figure 7:
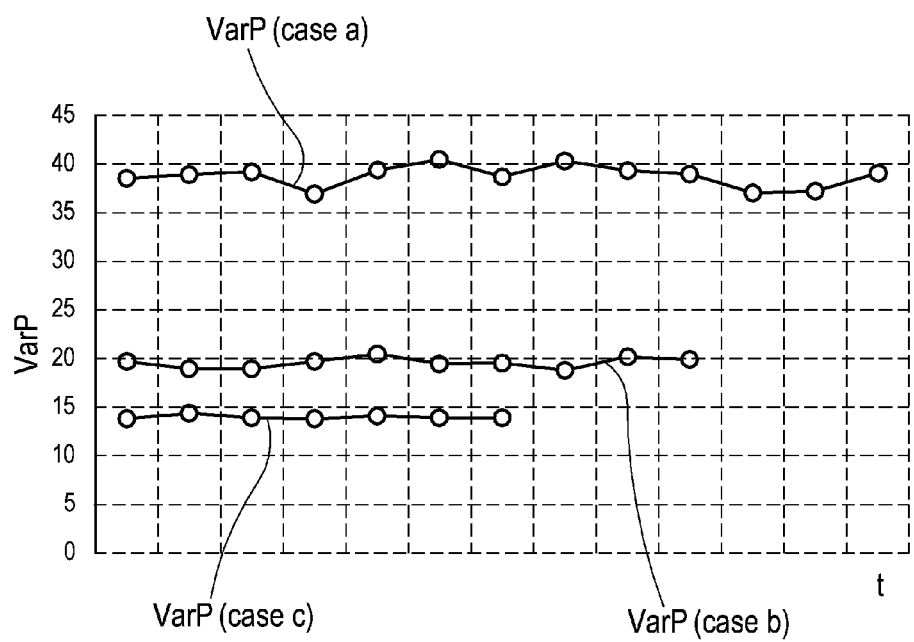
FIG. 7 is a time diagram which shows three progressions of the variance in arterial pressure in the arterial expansion chamber in the three respective conditions of FIG. 4.

As can in fact be understood from an analysis of the graph of FIG. 7, which represents, over time, the trends of the pressure variance VarP over time of the three conditions of standard level, median level and minimum level (or level of non-safety), in general the statistical indicator of dispersion (pure number) diminishes when the fluid level in the expansion chamber falls.

Thus a value of the statistical indicator which is lower than a threshold $T_h$ is a reliable index of minimum (or non-safety) level (or in any case an index of necessary attention on the part of the specialised personnel).

Obviously the statistical indicator related to the control value (and particularly the statistical variance VarP of the measured pressure values $P_j$) is calculated on a plurality n of measured pressure values $P_j$; in particular, n is greater than 6 and still more in particular n is at least equal to 10 with the purpose of eliminating the noise effects in the measurement. The value of n by way of example selected is 13.

In a further (but secondary) aspect, the reference threshold $T_h$ is a variable threshold, and in particular the reference threshold is updated in realtime during the treatment time, for example at each pressure measurement $P_j$.

The calculation of a variable threshold $T_h$ enables setting, as setting parameter, a specific probability of false alarm $P_{fa}$ and having the threshold $T_h$ such as to guarantee respect of the probability in each step of determining the occurrence of a condition of appreciable variation in the blood level in the expansion chamber 11, 12.

For this purpose it is provided (even though other possibilities of variable threshold calculation exist) to calculate the probability α of a type I error through of the following relation:

$$\alpha = 1 - \sqrt[K_n]{1 - P_{fa}}$$

in which:
$K_n$=number of measurements carried out during a treatment time ($T_{tot}$);
$P_{fa}$=set probability of detecting an erroneous change in blood level in the expansion chamber during a treatment time ($T_{tot}$).

At this point the variable reference threshold (Th) is defined by the following function:

$$T_h \text{VarP}_{ref} - t\alpha^* \sigma$$

in which:
'VarPref' is the mean of the variance of a number n of initial pressure values (Pj) measured at start of treatment; 'tα' is the confidence interval of a Student distribution of probability with n−1 degrees of freedom corresponding to the error α of type I;

'σ' is the standard deviation of the pressure variance calculated on a number n of sampled pressure data (Pj).

Thus, the reference threshold $T_h$ is a variable threshold according to one of more of the following variables: the oscillating pressure component ΔP(t), a dispersion index summarily describing a quantitative statistical distribution of the measured pressure values Pj, the standard deviation 6 of the pressure values measured $P_j$, the confidence interval to of a Student probability distribution, in particular with n−1 degrees of freedom corresponding to an error α of type I, the average VarP$_{ref}$ of the variance VarP of the pressure values measured $P_j$ in particular at the start of treatment time.

Where the control unit 21 establishes that the apparatus is in a condition of variation of blood level in any one of the expansion chambers 11, 12, through the comparison, an alarm situation is generated at least signalled by an acoustic and/or visual warning, so as to attract the attention of an operator who may verify the effective blood level and possibly correct the potentially dangerous situation.

Figure 8:
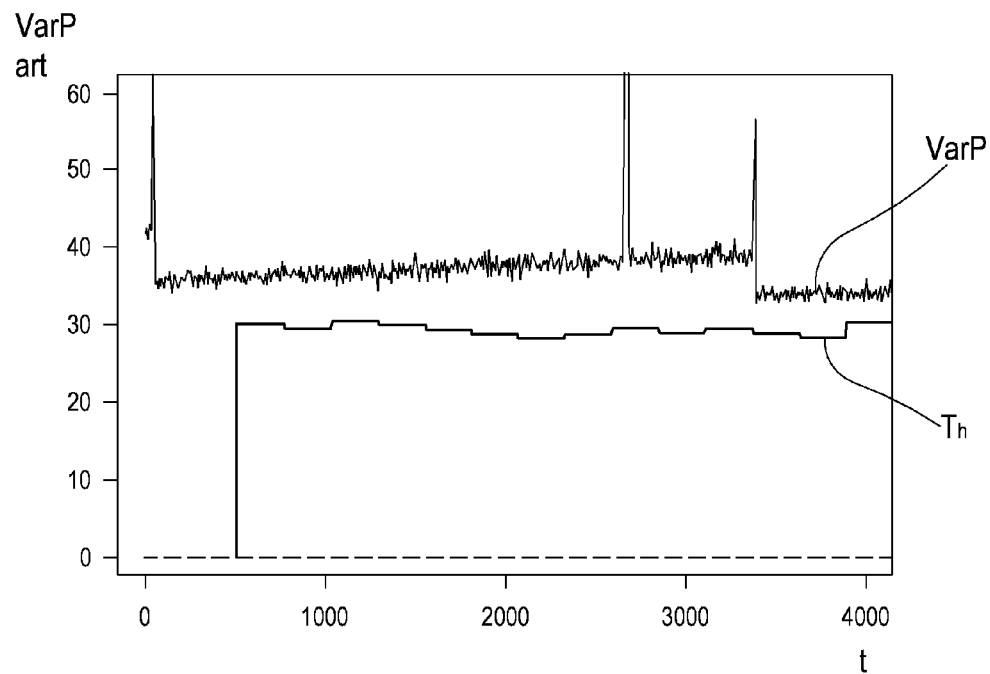
FIG. 8 shows a detail of the progression of the variance of the arterial pressure in the expansion chamber and also illustrates the variable threshold value in a situation of absence of alarm.

In particular FIG. 8 illustrates the progression of the statistical variance of pressure VarP at treatment instants and also the variable threshold $T_h$ in the corresponding instants, evidencing the variable progression over time of both. In figure the pressure variance is never below the threshold and thus there is no alarm generation.

Figure 9:
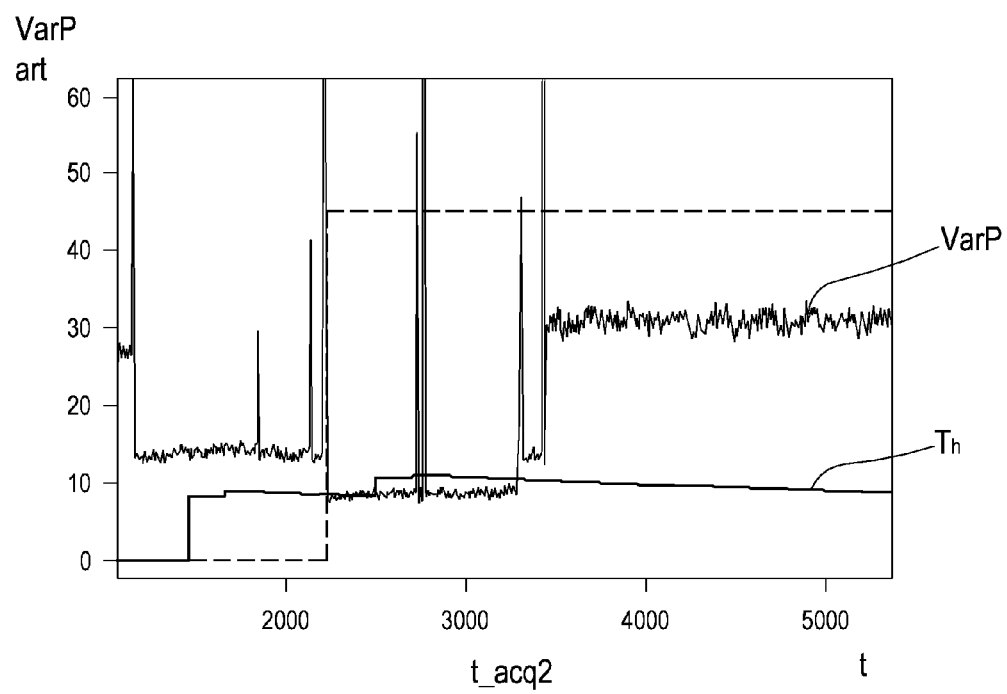
FIG. 9 shows a detail of the progression of the variance of the arterial pressure in the expansion chamber and also illustrates the variable threshold value in a situation where an alarm is present.
Figure 10:
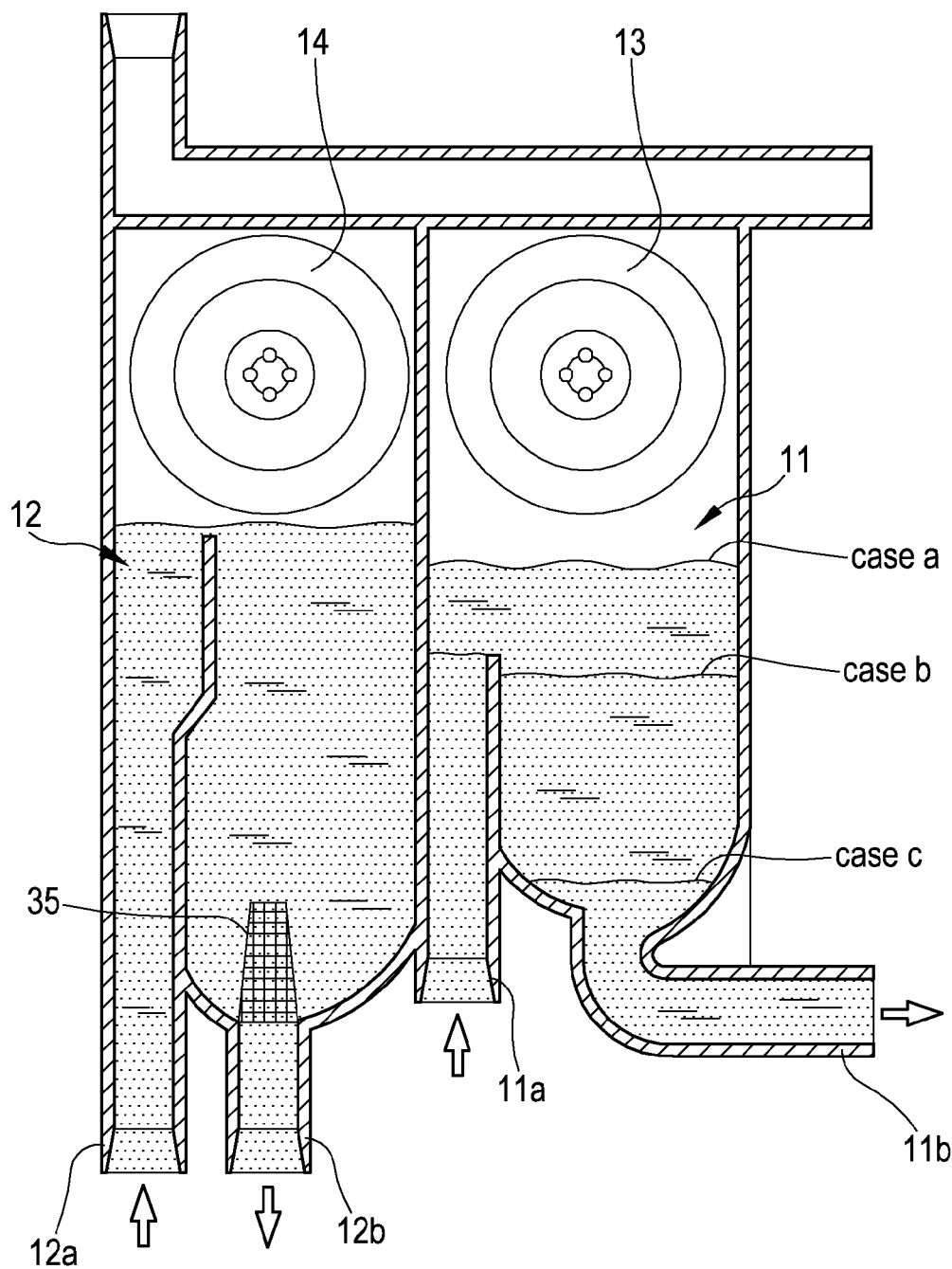
FIG. 10 shows a detail of the expansion chambers with the standard blood level (case a), average blood level (case b) and low blood level (case c) in the arterial chamber.

FIG. 9 illustrates the same variables as a function of the so time, in a situation in which the variance is for some time instants below the threshold and the apparatus therefore generates an alarm.

In more evolved apparatus the control unit 21 may be programmed such that in a case that a predetermined number of conditions of variation in the blood level in the expansion chamber 11, 12 obtains (or even one situation only), it commands the respective actuator 17, 18 in the chamber in which the problem has occurred such as to enable passage of gas through the ventilation opening 15, 16, re-establishing the correct blood level in the chamber.

In particular, since in general a low blood level occurs, the control unit commands the actuator 17, 18 to enable passage of gas in exit from the ventilation opening 15, 16.

In addition to or alternatively the control unit 21, in the event of a verification of a predetermined number of conditions of variance in the blood level in the arterial expansion chamber and/or venous chamber 11, 12, may command actuators that are at least active on the extracorporeal blood circuit 8 to place the patient in a situation of safety.

For example, the control unit 21 may command at least the blood pump 9 to reduce or zero the blood flow in the extracorporeal blood circuit 8 and substantially annul the passage of fluid through the semipermeable membrane 5 of the treatment unit 2 (if present).

Lastly the control unit 21 may also perform a consistency check of the detected and calculated values. In particular the control unit 21 may be programmed to compare the control value VarP calculated with at least one maximum admissible value VarP$_{max}$ and a minimum admissible value VarP$_{min}$ such as to determine whether the control value is within a correct functioning interval VarP≤VarP$_{max}$; VarP≥VarP$_{min}$ and to signal a malfunction in the event that the control value is not within the correct functioning value. In addition (or alternatively), the consistency check may be performed on the single measured pressure values $P_j$ by verifying whether a plurality thereof is out of a reasonable functioning range.

Indeed, the pressure sensor of the expansion chamber is substantially the only component of the apparatus (apart from the control unit) that is used for performing the verification function and the analyses mentioned above have the main aim of verifying a fault or a discrepancy that might invalidate the detection.

It is clear that the control unit 21 is programmed to perform the above-described steps in relation to the arterial expansion chamber 11 located on the blood return line 6 and/or in relation to the venous expansion chamber 12 located on the blood return line 7.

In particular, the use of this analysis in relation to the arterial chamber is proposed as usually the expansion chambers upstream of the treatment unit 2 are not provided with level sensors and/or other pre-unit safety systems 2 and therefore air that might enter the collecting line 6 is arranged to reach the treatment unit and be transformed into plurality of micro-bubbles thereby, thus becoming more difficult to detect downstream in the return line 7.

Obviously the described methodology is usable on each expansion chamber which might be present on the extracorporeal circuit (in addition to or in replacement for the described expansion chambers).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An apparatus for extracorporeal blood treatment comprising:
   at least a treatment unit having at least a first chamber and at least a second chamber separated from one another by a semipermeable membrane;
   at least a blood removal line connected to an inlet port of a first chamber and predisposed to remove blood from a patient;
   at least a blood return line connected to an outlet port from the first chamber and predisposed to return treated blood to the patient;
   at least an expansion chamber placed at least in one of the blood removal line and the blood return line, the expansion chamber being arranged in use to contain a predetermined quantity of gas in an upper portion and a predetermined quantity of blood at a predetermined level in a lower portion, the blood removal line, the blood return line, the first chamber and the at least an expansion chamber being part of an extracorporeal blood circuit;
   at least a blood pump operating at the extracorporeal blood circuit such as to move the blood in the circuit;
   at least a pressure sensor associated to the expansion chamber and configured such as to enable determining pressure values internally of the expansion chamber;
   at least a fluid evacuation line connected to an outlet port of the second chamber;
   a control unit connected to the at least a pressure sensor, with the pump, and configured to:
      move the blood pump such as to generate a variable blood flow comprising a constant flow component of a desired blood flow value and a variable flow component having a substantially nil mean value, the variable blood flow generating at least in the expansion chamber a pressure progression that is variable in time comprising a pressure component oscillating about a mean value;
      receive from the at least a sensor a plurality of pressure values for a time period comprising a plurality of pressure oscillations about the means value, the pressure values being measured at successive time instants;
      calculate, as a function of the pressure values, a control value that is representative of the oscillating pressure component,
      compare the control value representing the oscillating pressure component with a reference threshold, and
      determine, following the comparison, the occurrence or not of a condition of variation of the blood level in the expansion chamber.

2. The apparatus of claim 1, wherein the condition of level variation of the blood level in the expansion chamber occurs when the control value representing the oscillating pressure component is lower than the reference threshold.

3. The apparatus of claim 1, wherein the calculated control value representing the oscillating pressure component is a statistical indicator, the statistical indicator being a dispersion index summarily describing a quantitative statistical distribution of the measured pressure values.

4. The apparatus of claim 3, wherein a control value is an indicative measurement of distance of the pressure values from a central value identified with the mean pressure value of the pressure or with the pressure median.

5. The apparatus of claim 1, wherein the control value representing the oscillation pressure component is a function of the statistical variance of the measured pressure values and wherein the step of comparison is a step of comparing the statistical variance of the measured pressure values with a reference value.

6. The apparatus of claim 1, wherein the reference threshold is a variable threshold, the reference threshold is updated in real time during a treatment time.

7. The apparatus of claim 1, wherein the reference threshold is a variable threshold, the reference threshold is updated in real time during a treatment time at each pressure measurement.

8. The apparatus of claim 1, wherein the reference threshold is a variable threshold, the reference threshold is updated in real time during a treatment time, wherein the reference threshold reference is a variable threshold according to at least a parameter selected in the group consisting of a specific set probability of generation of a false alarm, the oscillating pressure component, a statistical dispersion index summarily describing a quantitative statistical distribution of the measured pressure values, the standard deviation of the measured pressure values, the confidence interval of a Student probability distribution and the mean of the variance of the measured pressure values.

9. The apparatus of claim 1, wherein the reference threshold is defined by the following function:

$$T_h = \mathrm{Var}P_{ref} - t\alpha * \sigma$$

wherein:
   '$\mathrm{Var}P_{ref}$' is the average of the variance of a number n of initial pressure values measured at start of treatment;
   '$t\alpha$' is the confidence interval of a Student distribution of probability with n−1 degrees of freedom corresponding to the error $\alpha$ of type I;
   '$\sigma$' is the standard deviation of the pressure variance calculated on a number n of sampled pressure data.

10. The apparatus of claim 1, wherein the control unit is programmed to perform the steps of receiving from the at least a sensor a plurality of pressure values for a time period comprising a plurality of pressure oscillations about the means value, the pressure values being measured at successive time instants; calculating, as a function of the pressure values, a control value that is representative of the oscillating pressure component; comparing the control value representing the oscillating pressure component with a reference threshold; and determining, following the comparison, the occurrence or not of a condition of variation of the blood level in the expansion chamber, in relation to an arterial expansion chamber located on the blood return line.

11. The apparatus of claim 10, wherein the control unit is programmed to perform the steps of receiving from the at least a sensor a plurality of pressure values for a time period comprising a plurality of pressure oscillations about the means value, the pressure values being measured at successive time instants; calculating, as a function of the pressure values, a control value that is representative of the oscillating pressure component; comparing the control value representing the oscillating pressure component with a reference threshold; and determining, following the comparison, the occurrence or not of a condition of variation of the blood level in the expansion chamber, in relation both to an arterial expansion chamber located on the blood removal line, and to a venous expansion chamber located on the blood return line.

12. The apparatus of claim 1, wherein the pressure sensor is located in the expansion chamber, at the portion arranged in use to contain the gas.

13. The apparatus of claim 1, wherein the expansion chamber exhibits a ventilation opening configured to enable, in use, a passage of gas from towards the expansion chamber, the apparatus further comprising at least an actuator operating on the ventilation opening to selectively prevent or enable passage of gas.

14. The apparatus of claim 13, wherein the ventilation opening is positioned at an upper portion of the expansion chamber arranged, in use, to be facing upwards and arranged to be always occupied by the gas, the control unit being programmed such that, in a case of verification of a predetermined number of conditions of appreciable variation of the blood level in the expansion chamber, the control unit commands the actuator to enable passage of gas through the ventilation opening.

15. The apparatus of claim 14, wherein the control unit is programmed such that, in the event of a verification of a predetermined number of conditions of level variation of blood in the expansion chamber, the control unit commands the actuator in order to enable passage of gas in outlet from the ventilation opening.

16. The apparatus of claim 1, wherein the control unit is programmed such that, in the event of verification of a predetermined number of conditions of variation of blood level in the expansion chamber, the control unit commands at least the blood pump to reduce or zero the blood flow in the extracorporeal blood circuit and substantially annuls the fluid passage through the semipermeable membrane of the treatment unit.

17. The apparatus of claim 16, further comprising two blood flow intercept organs active on the extracorporeal circuit, one downstream of a venous expansion chamber along the flow direction of the blood in the extracorporeal circuit, the other upstream of an arterial expansion chamber, each of the blood flow intercept organs comprising a respective clamp respectively active on the blood return line and on the blood removal line, the control unit being active on the intercept organs such as to command the intercepting or not of the flow, the control unit being programmed such that, in a case of verification of a predetermined number of conditions of variation of the blood level in the expansion chamber, the control unit commands the intercept organs of the blood flow to inhibit the passage of blood in the blood removal and/or blood return lines.

18. The apparatus of claim 1, wherein the control unit is programmed such as to compare the control value with at least a maximum admissible value and a minimum admissible value in order to determine whether the control value is internal of a correct functioning interval and in order to signal a malfunction in the event that a control value falls outside of a correct functioning interval.

* * * * *